(12) United States Patent
Parissaux et al.

(10) Patent No.: US 11,033,504 B2
(45) Date of Patent: Jun. 15, 2021

(54) FILM-FORMING COMPOSITIONS FOR THE FILM-COATING OF SOLID FORMS

(71) Applicant: ROQUETTE FRERES, Lestrem (FR)

(72) Inventors: Xavier Parissaux, St. Omer (FR); Gregory Le Bihan, Annezin (FR); Sebastien Croquet, Merville (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 16/055,815

(22) Filed: Aug. 6, 2018

(65) Prior Publication Data

US 2019/0038563 A1  Feb. 7, 2019

Related U.S. Application Data

(63) Continuation of application No. 14/780,862, filed as application No. PCT/FR2014/050737 on Mar. 28, 2014, now abandoned.

(30) Foreign Application Priority Data

Mar. 29, 2013  (FR) ..................... 13 52880

(51) Int. Cl.

| A61K 9/28 | (2006.01) |
| A23P 20/00 | (2016.01) |
| A23L 27/30 | (2016.01) |
| C09D 103/08 | (2006.01) |
| A61K 36/31 | (2006.01) |

(52) U.S. Cl.
CPC ............ *A61K 9/286* (2013.01); *A23L 27/34* (2016.08); *A23P 20/00* (2016.08); *A61K 9/2826* (2013.01); *A61K 9/2893* (2013.01); *A61K 36/31* (2013.01); *C09D 103/08* (2013.01); *A61K 9/282* (2013.01)

(58) Field of Classification Search
CPC .............................. A61K 9/2826; A61K 9/286
See application file for complete search history.

(56) References Cited

U.S. PATENT DOCUMENTS

| 6,375,981 B1 | 4/2002 | Gilleland et al. |
| 2002/0142031 A1 | 10/2002 | Gilleland et al. |
| 2005/0196436 A1* | 9/2005 | Chantranukul ...... A61K 9/4816 424/451 |
| 2007/0110799 A1* | 5/2007 | Leferve .................. A01N 25/10 424/451 |

FOREIGN PATENT DOCUMENTS

| CN | 1882317 | 12/2006 |
| CN | 1934181 | 3/2007 |
| CN | 10136443 | 1/2009 |
| JP | 2005112849 A | 4/2005 |

OTHER PUBLICATIONS

Chinese Office Action with English translation; Application No. 2014800180680.

* cited by examiner

*Primary Examiner* — Mark V Stevens

(57) ABSTRACT

The invention relates to a film-forming composition comprising a fluidised hydroxypropyl starch and sorbitol, and to a film-coating method using said composition. The invention further relates to film-coated solid forms comprising a fluidised hydroxypropyl starch and sorbitol in the coating.

17 Claims, 3 Drawing Sheets

FILM-FORMING COMPOSITIONS FOR THE FILM-COATING OF SOLID FORMS

CROSS-REFERENCE TO RELATED APPLICATIONS

This application is a Continuation Application of U.S. patent application Ser. No. 14/780,862, filed Sep. 28, 2015, which claims priority as a 371 National Filing of Application No. PCT/FR2014/050737, filed Mar. 28, 2014, which claims priority from FR Patent Application No. 13 52880, filed on Mar.29, 2013. The priority of said US, PCT and FR Patent Applications are claimed. Each of the prior mentioned applications is hereby incorporated by reference herein in its entirety.

A subject of the present invention is a film-forming composition comprising a fluidized hydroxypropyl starch and sorbitol, and said invention is also directed toward a film-coating process using such a composition.

A subject of the present invention is also film-coated solid forms comprising a fluidized hydroxypropyl starch and sorbitol in their film-coating.

PRIOR ART

Film-forming compositions are widely used in the pharmaceutical, cosmetics and food-processing industry, in particular for the film-coating of solid forms.

The film-coating of solid forms, in particular of tablets, is an operation which aims to obtain a physical and chemical protection of the active ingredients. The medicament is thus protected against its environment (moisture, oxygen, light). The film-coating also makes it possible to mask the taste, the odor or the color of the active ingredients, and also makes it possible to modify their rate of release in the organism by increasing the resistance of the tablet to gastric juices. Film-coating facilitates the ingestion of tablets, and improves their appearance and their mechanical integrity. Most solid forms can be film-coated: tablets, granules, gel capsules, seeds, confectionary products.

The film-coating consists of the application of a film-forming liquid composition on to a solid form, this composition becoming, after drying, a protective film.

The ideal film-forming agent should make it possible to obtain an elastic and cohesive film. It is preferably water-soluble, water being the preferred solvent as opposed to organic solvents because it is easy to use and is inoculus.

In order to make the films less brittle, a plasticizer is sometimes integrated into these film-forming compositions. The plasticizer lowers the glass transition temperature (Tg) of the film, it increases its flexibility, its resistance and its resilience, and facilitates the handling of the film-forming composition.

Starch is very widely used in the textile and paper industry as a film-forming agent. It is, on the other hand, used much less for applications in the film-coating field.

Despite tensile strengths comparable to those of certain synthetic polymers, starch-based materials in fact remain very fragile. They are in addition very sensitive to water: the amount of water contained in the films very considerably modifies the Tg and therefore the mechanical properties of the materials obtained. Other factors, such as the molar mass and the crystallinity, can play a role with regard to the properties of starch-based films.

Another difficulty is that, in the particular field of film-coating, the films are very thin, about a few tens of micrometers, and are subjected to particularly high stresses, which will promote cracking thereof.

Cracking of the film occurs in particular when the latter is too dehydrated, for example during the rapid drying of tablets at the time of the film-coating, or subsequently, in the case of tablets which take up the water contained in the film.

The film may also break during storage, when the ambient conditions promote swelling of the tablets, for example when they are placed in a humid atmosphere, at high temperature, and in particular when they do not have any packaging. This is particularly true for hygroscopic tablets, the volume of which significantly increases through absorption of the moisture from the air.

It is, moreover, necessary for the film-forming composition to be able to satisfy the other constraints associated with the problem of the film-coating, in particular for it to be able to adhere to the solid forms to be film-coated, for it to be non-reactive with respect to the ingredients which make up the solid forms, and for it to have a behavior suitable for machine operation (for example in terms of viscosity or of Tg).

Another difficulty is that solid forms to be film-coated differ in terms of composition and in terms of form and can therefore have extremely varied physicochemical characteristics, for example with regard to the hygroscopic nature, the hardness, the porosity, the surface energy, or else the solubility. It is therefore particularly difficult to find film-forming compositions suitable for the film-coating of all these solids forms.

There is at the current time no amylaceous film-forming composition which effectively solves all these problems. There is no "universal" film-forming composition for an application in film-coating.

As it happens, it is to the credit of the applicant to have succeeded in developing film-forming compositions that are particularly suitable for the film-coating of all sorts of solid forms. The cracking phenomena of the films are greatly reduced, or even eliminated, this being even for solid forms of which the volume varies greatly owing to water uptake or to thermal expansion.

The solution is based on the judicious identification of particular starch/plasticizer pairs which make it possible to obtain exceptional results in terms of plasticization. The starch selected by the applicant is in particular a fluidized hydroxypropyl starch, and the plasticizer used is sorbitol.

The results obtained by the applicant by choosing sorbitol as plasticizer and a fluidized hydroxypropyl starch as film-forming agent are exceptional, and are opposite to what the literature teaches.

Firstly, fluidized starches are known for their tendency to form films that are more brittle than those formed by native starches, owing to their lower molecular weight.

On the other hand, sorbitol has for more than ten years been considered to be a poor plasticizer for starch. Compared with glycerol, which is conventionally used, the literature teaches that sorbitol results in the formation of films that are more rigid and more friable, which has up until now reinforced those skilled in the art in the choice of glycerol as plasticizer for amylaceous materials.

Mention may, for example, be made of a study by Yachuan Zhang et al. (Plasticization' of Pea Starch Films with Monosaccharides and Polyols. Journal of food science, 10 Vol. 71, No. 6: 253-261 (2006)) on the plasticization of a pea starch, and a study by Aji P. Mathew et al. (Plasticized waxy maize starch: effect of polyols and relative humidity on material properties. Biomacromolecules, 3. 1101-1108 (2002)), on the plasticization of a waxy maize starch. These studies confirm the superiority of glycerol in the plasticization of amylaceous materials.

Other studies have even shown that, when sorbitol is used below certain contents, it exerts an anti-plasticizing effect.

For example, a study by S. Gaudin et al. (Plasticization and mobility in starch-sorbitol films. Journal of Cereal Science 29. 173-284 (1999)) describes the anti-plasticizing effect of sorbitol on wheat starch when it is used at a content below 27% by weight relative to the weight of starch.

A study by Suzana Mali et al. (Antiplasticizing effect of glycerol and sorbitol on the properties of cassava starch films. Braz. J. Food Technol., Vol. 11, No. 3, 194-200 (2008)), describes the anti-plasticizing effect of sorbitol on cassava starch at a content below 15% by weight, relative to the weight of starch.

As it happens, the applicant has shown that, by choosing a fluidized hydroxypropyl starch as film-forming agent, sorbitol exerts its plasticizing effect even below these contents, thus demonstrating the particularity of the starch/plasticizer pair identified by the applicant. Some documents exist, moreover, which report the use of amylaceous materials for applications in film-coating.

In its French patent FR 2 862 654 B1 for example, the applicant describes a film-coating composition using a stabilized legume starch plasticized with glycerol. These compositions already had, good properties compared with those of the prior art. However, the applicant demonstrated problems of cracking of the films which appear in certain cases, in particular on very hygroscopic tablets.

Sorbitol, moreover, was briefly described for its use in film-coating compositions.

Mention may, for example, be made of application WO 02/00205 regarding compositions using an acetylated waxy corn starch. It emerges from this application that no test for film-coating of solid forms is given for these compositions, since the preferential plasticizer was once again glycerol.

Patent application WO 02/092708 also describes amylaceous film-forming compositions comprising sorbitol, using a high-amylose corn starch as film-forming agent. However, the sorbitol was always used in combination with glycerol, and at extremely high contents. Sorbitol and glycerol thus each represented 50% of the weight of starch, i.e. these compositions comprised as much plasticizer as starch.

This further demonstrates the particularity of the starch/plasticizer combination identified by the applicant, since very good results were obtained, even using much lower sorbitol contents.

OBJECTIVES OF THE INVENTION

An object of the present invention is thus to provide novel film-forming amylaceous compositions, in particular for the film-coating of solid forms, which make it possible to reduce, or even eliminate, the problem of cracking of the films.

The invention makes it possible to solve the abovementioned problems by providing film-forming compositions that are easy to prepare and to use, cost a reasonable amount, make use of biobased materials, and are safe from the. point of view of the health of handlers and consumers.

DESCRIPTION

Figure 1C:
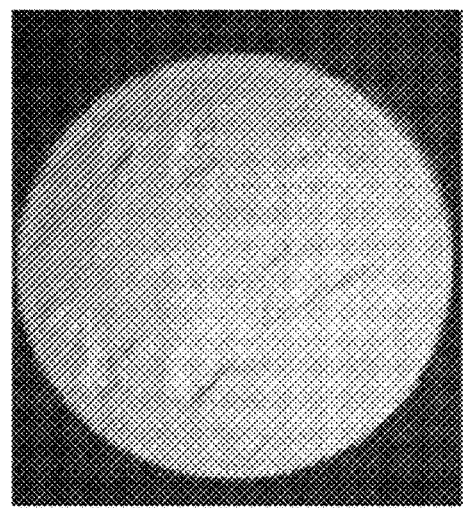
FIG. 1C shows the tablets film-coated with compositions C.

As shown in example 1, and contrary to what the prior art teaches, sorbitol makes it possible to lower the Tg of the amylaceous film at contents of about 5% by weight relative to the weight of starch. Contrary to what had therefore previously been noted, in the particular case of the starch chosen according to the present invention, not only does sorbitol exert a plasticizing effect at low contents, but it is in addition a better plasticizer than glycerol. Indeed, such performance levels are not observed as soon as the starch or the plasticizer used is modified, thereby demonstrating the importance of the judicious choice of the starch/plasticizer pair identified by the applicant.

The relevance of these low contents was confirmed for applications in film-coating. For plasticizer contents of about 8.6% by weight relative to the weight of starch, the film-forming compositions according to the invention resulted in the formation of a uniform and adherent film-coating layer when sorbitol was used, whereas cracking of the film-coating films occurred with glycerol (example 2a)).

In the film-forming compositions according to the invention, sorbitol can thus be introduced in contents of between 5% and 80% by weight relative to the weight of fluidized hydroxypropyl starch, in particular between 5% and 40% for applications in film-coating.

The sorbitol and the fluidized hydroxypropyl starch according to the invention have, moreover, the advantage of being able to be mixed in pulverulent form. Indeed, the plasticizers previously used in film-forming compositions, in particular glycerol, were always in liquid form. However, starch can be mixed with water only at the time of actual use of the film-forming composition. With the starch and the plasticizer identified by the applicant, it is possible to provide the film-forming composition according to the invention in the form of a ready-to-use product, so that a step of extemporaneous mixing of the starch and the plasticizer, during, for example, the film-coating of tablets, is no longer necessary.

Once it is in the form of an aqueous composition, i.e. in the form of a solution or of a suspension, the aqueous film-forming composition according to the invention has in addition the advantage of a low viscosity. It is thus possible to increase its solids content and therefore in parallel to reduce its water content. As a result of this, the films obtained are easier to dry, and the times and costs required for the manufacture thereof are significantly reduced. A first subject of the present invention is thus a film-forming composition, in particular intended for the film-coating of solid forms, characterized in that it comprises a fluidized hydroxypropyl starch and sorbitol.

For the purposes of the present invention, the term "film-forming composition" is intended to mean a composition comprising at least one polymer (film-forming agent), capable of forming an essentially continuous film in the presence of a solvent, in particular of water. It is in particular an amylaceous film-forming composition, i.e. using a starch as film-forming agent.

For the purposes of the present invention, the term "starch" is intended to mean the starch extracted, or in other words isolated, by any suitable technique known to those skilled in the art, from an amylaceous source, such as leguminous plants, cereals or tuberous plants. The starch may, for example, be a pea starch, corn starch or potato starch, or a starch of a mixture thereof.

For the purposes of the present invention, the term "hydroxypropyl starch" is intended to mean a starch substituted with hydroxypropyl groups by any technique known to those skilled in the art, for example by etherification reaction with propylene oxide, having in particular a hydroxypropyl group content of between 0.1% and 50% by dry weight relative to the dry weight of hydroxypropyl starch, preferentially between 1% and 15%, more preferentially between 5% and 9%, and in particular close to 7%. This content is in particular determined by proton nuclear magnetic resonance spectrometry, in particular according to standard EN ISO 11543:2002 F.

For the purposes of the present invention, the term "fluidized starch" is intended to mean a starch which has undergone a hydrolysis operation, i.e. an operation aimed at reducing its average molecular weight. Those skilled in the art know how to obtain such starches, for example by chemical treatments such as oxidation and acid treatments, or else by enzymatic treatments. Those skilled in the art will naturally adjust the level of fluidization of the starch, according to the viscosity desired for the film-forming composition.

Preferentially, the fluidized hydroxypropyl starch according to the invention has a weight-average molecular weight of less than 2 000 000 Da, preferentially greater than 20 000 Da, preferentially between 100 000 and 1 000 000 Da, quite preferentially between 500 000 and 600 000 Da.

This weight-average molecular weight can be determined by those skilled in the art using size exclusion chromatography of the HPSEC-MALLS type (High Performance Size Exclusion Chromatography coupled on-line with Multiple Angle Laser Light Scattering).

This weight can be measured by size exclusion chromatography, according to the following protocol:
  preparation of a sample by solubilization of the fluidized hydroxypropyl starch, by heating at 100° C. for 30 min in a diluting solvent consisting of a DMSO/NaNO$_3$ mixture (0.1M of NaNO$_3$ in DMSO), it being possible for said sample to have a concentration ranging from 2 to 10 mg of starch per ml of diluting solvent;
  use of a high performance liquid chromatography (HPLC) apparatus equipped with a pump, operating in isocratic mode, circulating an elution solvent at 0.3 ml/min, with a refractometer, with an 18-angle multiple angle light scattering laser detector heated to 35° C., for example a Dawn Heleos detector from the company Wyatt, and with an oven for thermostatic control of the columns heated to 35° C., for example equipped with polyhydroxymethacrylate columns of Suprema type and for which the elution solvent is, for example, a 0.1M aqueous sodium nitrate solution containing 0.02% by weight of sodium azide;
  injection into the device of a sample volume of approximately 100 µl.

The weight-average molecular weights can be determined from the spectra obtained, for example by reprocessing the spectra in 1st order exponential using an analytical software of Astra v.5 type. The molecular weights are conventionally distributed according to a Gaussian curve, the weight-average molecular weight being close to the median.

The film-forming composition according to the invention is preferentially characterized in that the fluidized hydroxypropyl starch is a legume starch and/or a corn starch.

More preferentially, the fluidized hydroxypropyl starch according to the invention is a legume starch, preferably a pea starch, more preferentially a smooth pea starch.

When the starch according to the invention is a pea starch, in particular a smooth pea starch, the starch in particular has an amylose content of between 25% and 45%, preferably between 30% and 44%, even more preferentially between 35% and 40%, and even better still between 35% and 38%, these percentages being expressed by dry weight relative to the dry weight of pea starch, and determined before fluidization and hydroxypropylation of said starch.

Preferentially, the film-forming composition according to the invention is characterized in that the sorbitol is included in said film-forming composition at a content of between 5% and 80% by dry weight relative to the dry weight of fluidized hydroxypropyl starch, preferentially between 5% and 40%, and more preferentially between 15% and 35%, the limit at 35% being preferentially excluded.

It should be noted that, in the present application, the contents of the various compounds are expressed as a function of the total solids content of the film-forming composition, with the exception of the sorbitol contents, which, unless otherwise indicated, are expressed as a function of the dry weight of starch. Indeed, it is the ratio of the film-forming agent to the plasticizer which determines in particular the quality of the plasticization and therefore of the film formed.

Advantageously, the film-forming composition according to the invention is characterized in that the fluidized hydroxypropyl starch and the sorbitol together represent between 15% and 100% by dry weight relative to the total weight of the solids of said film-forming composition, preferentially between 30% and 95%, and more preferentially between 60% and 95%.

Preferentially, the film-forming composition according to the invention is characterized in that it is a ready-to-use product.

For the purposes of the present invention, the term "ready-to-use product" is intended to mean a pulverulent composition, in particular intended for the film-coating of solid forms. The ready-to-use product can be prepared by any suitable mixing means known to those skilled in the art, for example using a powder mixer.

In a second advantageous embodiment, the film-forming composition according to the invention is characterized in that it is an aqueous composition. The aqueous film-forming composition according to the invention is preferentially characterized in that it has a solids content of between 5% and 50% by weight, preferentially between 10% and 35%, more preferentially between 15% and 30%.

It advantageously has a viscosity, measured at 25° C., of less than or equal to 500 mPa·s, more preferentially of between 50 and 500 mPa·s, more preferably between 80 and 300 mPa·s.

This viscosity, in the present invention, is a Brookfield viscosity determined by means of a Brookfield RVF 100 viscometer, using the spindle of the apparatus which gives a reading of between 20% and 80% of the scale of the dial of the apparatus, at a rotational speed of 100 revolutions per minute.

Generally, and entirely advantageously, the aqueous film-forming composition or the ready-to-use product according to the invention comprise additives conventionally used by those skilled in the art, in particular in the film-coating field, in particular chosen from:
- antiaggregants, in particular fatty substances such as glycerol derivatives, for example glyceryl monostearate, sugar esters, magnesium stearate, kaolin and stearic acid;
- opacifiers, in particular mineral materials, such as titanium dioxide or calcium carbonate;
- pigments and dyes, for example soluble dyes or aluminum lakes, such as E129, E132, E133, E110 or E102, pigments such as iron oxides, dyes of natural origin, such as carminic acid or a copper-chlorophyll complex;
- flavorings or sweeteners, for example mint oil, aspartame and acesulfame;
- compounds for improving shininess, for example medium-chain triglycerides.

Preferentially, the film-forming composition according to the invention comprises at least one antiaggregating additive, preferentially stearic acid.

Preferentially, the film-forming composition according to the invention comprises at least one opacifying additive, preferentially titanium dioxide.

The film-forming composition according to the invention may, moreover, comprise:
- film-forming agents other than the fluidized hydroxypropyl starch used in accordance with the invention, for example synthetic polymers, such as hydroxypropylmethylcellulose (HPMC), hydroxypropylcellulose (HPC) or polyvinyl alcohol (PVA),
- and/or plasticizers other than the sorbitol according to the invention, for example sorbitol derivatives, in particular anhydrides of sorbitol, glycerol, polyethylene glycol, triethyl citrate, polysorbate, carnauba wax and hydrogenated castor oil.

Preferentially, the film-forming composition according to the invention comprises less than 80% of film-forming agent other than the fluidized hydroxypropyl starch according to the invention, preferentially less than 70%, preferentially less than 60%, preferentially less than 50%, preferentially less than 40%, preferentially less than 30%, preferentially less than 20%, preferentially less than 10%; these percentages being expressed by dry weight, relative to the total dry weight of film-forming agent of the film-forming composition.

Likewise, since the sorbitol according to the invention is by itself an excellent plasticizer for the fluidized hydroxypropyl starch according to the invention, the presence of other plasticizers is optional. Thus, preferentially, the film-forming composition according to the invention comprises less than 80% of plasticizers other than sorbitol, preferentially less than 70%, preferentially less than 60%, preferentially less than 50%, preferentially less than 40%, preferentially less than 30%, preferentially less than 20%, preferentially less than 10%; these percentages being expressed by dry weight, relative to the total dry weight of plasticizer of the film-forming composition.

For reasons of ease of processing, it is preferable to minimize the amount of raw materials to be handled.

Thus, preferentially, the fluidized hydroxypropyl starch and the sorbitol represent, in the film-forming composition according to the invention, most, and preferentially all, of the film-forming agents and of the plasticizers, respectively.

The fluidized hydroxypropyl starch of the film-forming composition according to the invention may also exhibit other modifications, and may for example have undergone physical treatments, in particular chosen from known precooking, cooking, extrusion, spray-drying or drying operations, microwave or ultrasonic treatment operations, plasticizing operations or granulation operations.

In particular, starch after hydroxypropylation and fluidization often comprises a portion of starch which has remained in granular form, i.e. which does not necessarily participate in the formation of the film.

It will therefore be preferable to make this portion of starch soluble in water, in order for the film-forming composition to contain a maximum of starch available for the formation of the film.

Thus, entirely advantageously, the starch according to the invention is characterized in that it is made soluble. It can be made soluble by any technique known to those skilled in the art, in particular by heat and/or mechanical treatment, for example by an operation of cooking in an aqueous medium, optionally followed by a drying step when it is desired to obtain a pulverulent product. The operation aimed at making the starch soluble can take place before the introduction of said starch into the film-forming composition, equally before or after the hydroxypropylation and/or the fluidization of the starch, or else after the introduction thereof into the film-forming composition, for example by cooking the film-forming composition at the time it is used.

Although the sorbitol according to the invention is preferentially a pulverulent sorbitol, for example such as those sold by the applicant under the name Neosorb® P60W, it may also be a crystallizable or non-crystallizable liquid sorbitol.

The film-forming composition in accordance with the invention is advantageously used for the film-coating of solid forms.

For the purposes of the present invention, the term "solid form" is intended to mean any presentation of food, pharmaceutical, cosmetic, chemical or agrochemical substances intended to undergo a film-coating operation. Examples of solid forms are tablets, gel capsules, capsules, pellets, microspheres, granules, seeds, solid food forms such as cookies, breakfast cereals, confectionary products (chewing gums, hard boiled candies, jelly confections), or else products in the form of powders and/or of crystals. When these solid forms are film-coated, they then include in their structure at least one film-coating layer, and the initial solid form is then denoted by the term "core".

To carry out the film-coating of solid forms, use may be made of any technique known to those skilled in the art, such as spray-drying in a fluidized bed, or in a conventional or perforated turbine.

Thus, a subject of the present invention is also a film-coating process, characterized in that it comprises:
- a step a') of spraying an aqueous film-forming composition according to the invention on to a moving bed of solid forms,
- a step b) of drying the solid forms thus film-coated, preferentially concomitant with step a').

A subject of the present invention is in particular a film-coating process, characterized in that it comprises:
- a step a) of producing an aqueous film-forming composition according to the invention, comprising mixing a ready-to-use product according to the invention with water,
- a step a') of spraying the aqueous film-forming composition obtained in step a) on to a moving bed of solid forms, a step b) of drying the solid forms thus film-coated, preferentially concomitant with step a').

As shown in examples 2 to 3, the aqueous film-forming composition can be sprayed on to a bed of tablets that has been preheated to a temperature of about 35° C. Conversely, in the processes described in patent FR 2 862 654 B1, the film-forming compositions plasticized with glycerol were sprayed on to a bed of tablets that was preheated to 55° C. This is particularly advantageous since this means that the working temperature can be significantly lowered. It results from this that, in addition to the reductions in energy costs, it is possible to film-coat temperature-sensitive tablets without problem.

Thus, preferentially, the process according to the invention is characterized in that the bed of solid forms is preheated to a temperature of between 30 and 60° C., preferentially between 30 and 40° C., in particular of about 35° C.

Preferentially, the gain in weight of the solid forms obtained after film-coating is between 1% and 10%, preferentially between 2% and 6%.

A subject of the present invention is also a solid form comprising a core covered with at least one film-coating layer, characterized in that this film-coating layer comprises a fluidized hydroxypropyl starch and sorbitol.

Advantageously, the fluidized hydroxypropyl starch is a legume starch and/or a corn starch, preferably a pea starch, more preferentially a smooth pea starch.

Particularly advantageously, the sorbitol is included in the film-coating layer at a content of between 5% and 80% by dry weight relative to the dry weight of fluidized hydroxypropyl starch, preferentially of between 5% and 40%, more preferentially between 15% and 35%, the limit at 35% being preferentially excluded.

Advantageously, the fluidized hydroxypropyl starch and the sorbitol together represent between 15% and 100% by dry weight relative to the total weight of the solids of the film-coating layer, preferentially between 30% and 95%, more preferentially between 60% and 95%.

Advantageously, the film-coating layer of the solid form according to the invention has an average thickness of between 10 and 90 µm, more preferentially between 20 and 60 µm, and even more preferentially between 25 and 55 µm.

Advantageously, the core of the film-coated solid form is a tablet.

The core according to the invention preferentially comprises at least one ingredient of interest, in particular agricultural, food, cosmetic or pharmaceutical interest.

The film-forming composition according to the invention is also particularly suitable for producing films.

The term "film" is intended to mean herein a thin and flat product, having an essentially planar surface, and a thickness of between 5 and 3000 µm, preferentially between 20 and 200 µm, more preferentially between 50 and 90 µm, and the thickness of which is relatively small in comparison to its length and its width. There are in particular films that can be grasped with the fingers. This includes food, pharmaceutical or cosmetic films. They are preferentially orodispersible films, but they may also be films intended for any other application in which the obtaining of a film with such a thickness is advantageous, for example of films with a support, such as transdermal patches for the administration of an active ingredient by application of the patch to the skin, of topical pharmaceutical or cosmetic films to be placed on the skin, such as films intended to be dissolved, for example in cosmetic, compositions, foods or beverages.

Thus, a subject of the present invention is also a process for producing films, characterized in that it comprises a step a) of spreading an aqueous film-forming composition according to the invention, and a step b) of drying the solution thus spread.

Step a) can be carried out by any technique known to those skilled in the art, for example by spreading a small and constant thickness of the solution on a planar or cylindrical surface, followed by drying at ambient temperature or under hot conditions.

A subject of the present invention is also a film, characterized in that it comprises a fluidized hydroxypropyl starch and sorbitol.

Advantageously, the fluidized hydroxypropyl starch is a legume starch and/or a corn starch, preferably a pea starch, more preferentially a smooth pea starch.

Particularly advantageously, the sorbitol is included in the film at a content of between 5% and 80% by dry weight relative to the dry weight of fluidized hydroxypropyl starch, preferentially of between 5% and 40%, more preferentially between 15% and 35%, the limit at 35% being preferentially excluded.

Advantageously, the fluidized hydroxypropyl starch and the sorbitol together represent between 15% and 100% by dry weight relative to the total weight of the solids of the film, preferably between 30% and 95%, more preferentially between 60% and 95%.

The composition according to the invention can moreover be used for the preparation of soft capsules, of hard gel capsules or of "caplets".

A subject of the present invention is thus also a process for producing tops and/or bodies of gel capsules, and/or a process for producing soft capsules, characterized in that it comprises a forming step using an aqueous film-forming composition according to the invention.

A subject of the present invention is also a process for producing caplets, characterized in that it comprises the immersion of solid forms in an aqueous film-forming composition according to the invention.

For the production of gel capsules, use may be made of conventional equipment, which consists in immersing metal fingers into the aqueous film-forming composition held at a constant temperature. For the production of soft capsules, use may be made of the known techniques of forming on drums or by extrusion. "Caplets" are produced, for example, by immersion of the tablets mechanically or by hand in a bath containing the aqueous film-forming composition according to the invention.

The examples hereinafter are an integral part of the present invention and serve to illustrate it without, however, constituting a limitation thereof.

EXAMPLES

Example 1

Plasticizing Effect of Sorbitol on a Fluidized Hydroxypropyl Starch

Several film-forming compositions with a 10% solids content are prepared. For each composition, 3 g are sampled and poured into a petri dish 55 mm in diameter. For drying, the films are left at ambient temperature for 72 h.

In order to analyze the quality of the plasticization, the glass transition temperature (Tg) of each film is measured after storage thereof at 66% relative humidity (RH) in a desiccator comprising a solution supersaturated with $NaNO_2$.

To measure the Tg, the films are weighed in non-pierced 40 µl aluminum crucibles, and are analyzed by differential thermal analysis (DTA), using the TA Instruments Q20 device, according to cycles of heating from −90° C. to 120° C., at 10° C./min, and of cooling from 120° C. to −90° C., at 20° C./min.

The Tg results obtained are given in the following table:

| | Content of plasticizer (sorbitol or glycerol) used for producing the film, by dry weight relative to the dry weight of starch | | | | | | | |
|---|---|---|---|---|---|---|---|---|
| | 0% | 2.5% | 5% | 7% | 10% | 20% | 30% | 40% |
| Fluidized hydroxypropyl pea starch + sorbitol | 67° C. | 65° C. | 39° C. | 3° C. | −36° C. | −34° C. | −37° C. | −42° C. |
| Fluidized hydroxypropyl pea starch + glycerol | 67° C. | 66° C. | 67° C. | 51° C. | 34° C. | 19° C. | 4° C. | −22° C. |
| Native pea starch + sorbitol | 75° C. | 73° C. | 75° C. | 74° C. | 59° C. | 38° C. | 21° C. | 10° C. |
| Hydroxypropyl pea starch + sorbitol | 74° C. | 75° C. | 75° C. | 68° C. | 41° C. | 19° C. | −3° C. | −21° C. |

The fluidized hydroxypropyl pea starch is in this case a pregelatinized starch having a hydroxypropyl group content of 6.8%.

The role of the plasticizer is to lower the Tg of the film formed by the film-forming agent. For a fluidized hydroxypropyl starch, the addition of 5% of sorbitol by dry weight relative to the dry weight of starch is sufficient to decrease the Tg.

Thus, contrary to what the prior art teaches, the sorbitol makes it possible to plasticize the starch even at low contents, i.e. of about 5% by dry weight relative to the dry weight of starch.

Moreover, these performance levels are not found as soon as the nature of the plasticizer or of the starch used is modified. Thus, no decrease in the Tg is observed in the comparative examples, for contents of about 5% of plasticizer.

Finally, even above 5% of plasticizer, in particular between 5% and 40%, it is still the film-forming composition according to the invention which makes it possible to obtain the best performance levels, i.e. the lowest Tg.

Thus, the film-forming composition according to the invention will advantageously be used at sorbitol contents of about 5% by dry weight relative to the dry weight of fluidized hydroxypropyl starch, in particular between 10% and 40%.

This study clearly shows that the excellent results obtained with the compositions according to the invention are the result of the specific choice of the film-forming agent/plasticizer pair identified by the applicant, in particular because the starch chosen is a hydroxypropyl fluidized starch, and because the plasticizer chosen is sorbitol.

Example 2

Film-Coating of Multivitamin Tablets

Example 2.a)—Comparison of Film-Forming Compositions According to the Invention with a Film-Forming Composition Using Glycerol as Plasticizer Three film-forming compositions A, B and C are prepared as follows:

| | A | B | C |
|---|---|---|---|
| Pregelatinized fluidized hydroxypropyl pea starch (hydroxypropyl group content = 6.8%) | 58% | 58% | 58% |
| Pigment/opacifier mixture (Spectracol Yellow, Sensient) | / | 22% | 22% |
| Titanium dioxide (Kronos, Kronos Titan GmbH) | 22% | / | / |
| Stearic acid (Stéarineries Dubois) | 15% | 15% | 15% |
| Sorbitol (Neosorb ® P60W, Roquette Frères) | 5% (i.e. 8.6% by dry weight relative to the dry weight of starch) | | / |
| Glycerol (G6279-1L, Sigma Aldrich) | / | | 5% | the percentages being expressed in dry weight relative to the total weight of solids.

Demineralized water is then added so as to obtain compositions containing 20% of solids.

The measured Brookfield viscosity of compositions A and B is between 100 and 150 mPa·s.

Biconvex round mineral multivitamin tablets, having an average weight of 600 mg, an average diameter of 11.3 mm and an average thickness of 6.3 mm, are film-coated with composition A, B or C.

The film-coating is carried out by spraying the aqueous composition using the following equipment:
Full turbine: Dumoulin TW 360 (30 cm in diameter), equipped with a hot air blowing system and a suction system.
Nozzle: Sinks 460.
Perastaltic pump: model Watson Marlow 323, pump head: 313 DW (3 rollers).
Exacanal tube (int. diam: 2 mm, ext. diam: 6 mm).
8 anti-slip bars.

The operating conditions are given in the following table:

| | A | B | D |
|---|---|---|---|
| Amount of tablets (kg) | | 1 | |
| Rotational speed (rpm) | | 16 | |
| Number of spray guns | | 1 | |
| Operating air pressure (bar) | | 4 | |

-continued

|  | A | B | D |
|---|---|---|---|
| Air inlet temperature (° C.) | 55 | 20 | 55 |
| Tablet bed temperature (° C.) | 36-38 | 20-22 | 36-38 |
| Spray flow rate (g/min) | 2-3.4 | 1.25-2 | 2-3.4 |
| Spraying time (min) | 72 | 121 | 70 |
| Weight gain (%) | 5 | 5 | 3 |

The film-coated tablets are placed under conditions which promote deformation thereof. They are incubated without packaging at 40° C. at 70% relative humidity (75% RH).

Figure 1B:
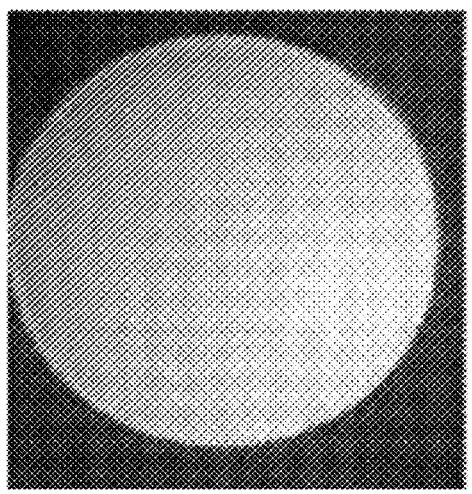
FIG. 1B shows the tablets film-coated with compositions B.
Figure 1A:
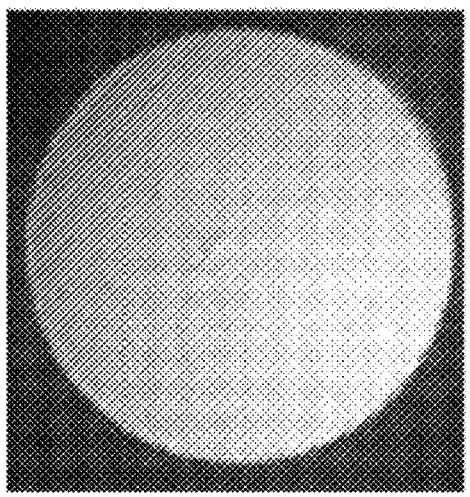
FIG. 1A shows the tablets film-coated with compositions A.

The results are given in FIGS. 1A-1C, which show tablets corresponding to the tablets film-coated with compositions A, B and C, respectively.

After incubation for one day, wide cracks in the film-coating films were observed for the tablets film-coated with composition C. No cracking occurred on the film-coated tablets with compositions A or B according to the invention, even after 5 days of incubation.

Film-forming compositions A and B have a sorbitol content of 8.6% by weight relative to the weight of fluidized hydroxypropyl starch, sorbitol being the only plasticizer of the film-forming composition.

As it happens, the tablets film-coated by means of these compositions have a film-coating which is entirely satisfactory, uniform and adherent, contrary to what is observed with a composition using the same contents of glycerol.

Moreover, the applicant also prepared a composition in which the fluidized hydroxypropyl pea starch of composition A was replaced with an equal content of hydroxypropyl (hydroxypropyl group content =6.8%), but non-fluidized, starch. These compositions proved to be impossible to use, since they had a viscosity that was much too high.

These tests thus confirm the results given in example 1, for applications in film-coating, and in particular (i) the superiority of sorbitol compared with glycerol, and (ii) its possible use at contents below 10%, in particular of about 8.6%, when the starch to be plasticized is a fluidized hydroxypropyl starch.

Example 2.b)—Comparison of a Film-Forming Composition According to the Invention Using a Sorbitol/Glycerol Mixture as Plasticizer, with Film-Forming Compositions Comprising a Glycerol/Lecithin Mixture Several film-forming compositions are prepared as follows:

|  | A | B | C |
|---|---|---|---|
| Pregelatinized fluidized hydroxypropyl pea starch (hydroxypropyl group content = 6.8%) | 52.7 | 62 | 52.7 |
| Stearic acid (Stéarineries Dubois) | 10.2 | 12 | 10.2 |
| Titanium dioxide (Kronos, Kronos Titan GmbH) | 12.75 | 15 | 12.75 |
| Yellow iron oxide (Neelikon Food Dyes and Chemicals Ltd) | 0.85 | 1 | 0.85 |
| Soyabean lecithin (Phospholipon S20, Lipoid) | 4.25 | 5 | 19.25 |
| Glycerol (G6279-1L, Sigma Aldrich) | 4.25 | 5 | 4.25 |
| Sorbitol (Neosorb ® P60W, Roquette Frères) | 15 | / | / | the percentages being expressed by dry weight relative to the total weight of solids.

Demineralized water is then added so as to obtain compositions containing 20% of solids.

The three compositions A, B and C thus comprise 8.1% of glycerol by dry weight relative to the dry weight of starch.

Composition A according to the invention comprises, in addition, 28.5% of sorbitol and 8.1% of lecithin, the sorbitol representing approximately 64% by dry weight of the total plasticizers.

Composition B differs from composition A in that sorbitol is absent. Composition C differs from composition A in that the sorbitol part has been replaced with lecithin.

Oblong mineral multivitamin tablets, having an average weight of 914 mg, an average length of 16.3 mm, an average width of 9.3 mm and an average thickness of 7.0 mm, are film-coated with composition A, B or C.

The film-coating is carried out by spraying the aqueous composition with the same equipment as that of example 2.a).

The operating conditions are given in the following table:

| Amount of tablets (kg) | 1.0 |
|---|---|
| Rotational speed (rpm) | 12 |
| Number of spray guns | 1 |
| Operating air pressure (bar) | 4 |
| Air inlet temperature (° C.) | 55 |
| Tablet bed temperature (° C.) | 32 |
| Spray flow rate (g/min) | 2.9 |
| Spraying time (min) | 51 |
| Weight gain (%) | 3.0 |

The film-coated tablets are placed under conditions which promote deformation thereof. They are incubated without packaging at 40° C. at 75% RH.

After one day of incubation, wide cracks in the film-coating films were observed for the tablets film-coated with composition B. Small cracks were observed on the tablets film-coated with composition C after one week of incubation. No cracking occurred on the tablets film-coated with composition A according to the invention, even after 2 weeks of incubation.

These results demonstrate the advantage of the use of sorbitol as a mixture with glycerol for plasticizing a fluidized hydroxypropyl starch, compared with the use of lecithin.

Example 3

Film-Coating of (Strongly Hygroscopic) Maca Tablets

For the film-coating of strongly hygroscopic tablets, oblong Maca tablets, having an average weight of 758 mg, an average length of 16.6 mm, an average width of 9.2 mm and an average thickness of 7.0 mm, are used. After multiple studies, the applicant in fact succeeded in demonstrating that the recurrent phenomena of cracking of the films observed on these tablets were due to their tendency to deform and to increase in volume to a particularly large degree.

In the tests which follow, the same deformation (in particular in terms of thickness, of length and of width) were measured for the film-coated tablets, whatever the film-coating composition tested. Thus, it is indeed the strength of the film which is tested.

Example 3.a)—Comparison of Film-Forming Compositions According to the Invention with Film-Forming Compositions Using Other Plasticizers Several film-forming compositions are prepared as follows:

|  |  | A | B | C |
|---|---|---|---|---|
| Pregelatinized fluidized hydroxypropyl pea starch (hydroxypropyl group content = 6.8%) |  | 60% | 68.75% | 57.3% |
| Stearic acid (Stéarineries Dubois) |  | 10% | / | / |
| Nacrous pigment (Sensipearl gold, Sensient) |  | 9.8% | 24% | 20% |
| Yellow pigment (Yellow lake, Silesia) |  | 0.2% | 1% | 0.8% |
| Plant magnesium stearate (Barlocher) |  | / | 6.25% | 5.2% |
| Soyabean lecithin (Phospholipon S20, Lipoid) |  | / | / | 16.7% |
| Sorbitol (Neosorb®) P60W, Roquette Frères | By weight relative to solids i.e. by weight relative to the starch | 20% 33% | / / | / / | the percentages being expressed, unless otherwise indicated, by dry weight relative to the total weight of solids.

Demineralized water is then added so as to obtain compositions at 20% of solids.

The film-coating of the Maca tablets with compositions A, B or C is carried out by spraying the aqueous composition with the same equipment as that of example 2.a).

The operating conditions are given in the following table:

| Amount of tablets (kg) | 1.0 |
|---|---|
| Rotational speed (rpm) | 12 |
| Number of spray guns | 1 |
| Operating pressure (bar) | 4 |
| Air inlet temperature (° C.) | 56 |
| Tablet bed temperature (° C.) | 35 |
| Spray flow rate (g/min) | 2.9 |
| Spraying time (min) | 51 |
| Weight gain (%) | 3.0 |

The film-coated tablets are then placed under conditions which promote deformation thereof. They are incubated without packaging at 40° C. and 75% RH for 5 days.

Figure 2C:
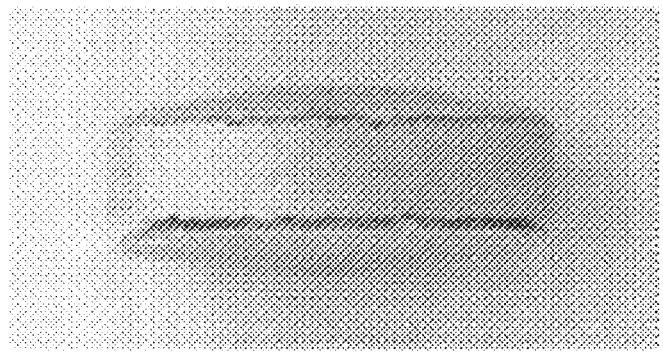
FIG. 2C shows the tablets film-coated with compositions C.
Figure 2B:
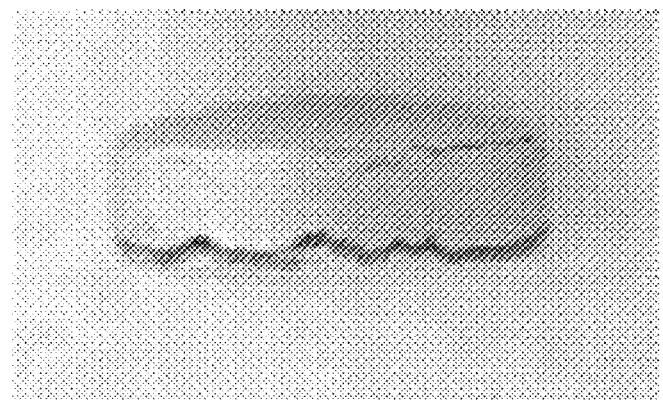
FIG. 2B shows the tablets film-coated with compositions B.
Figure 2A:
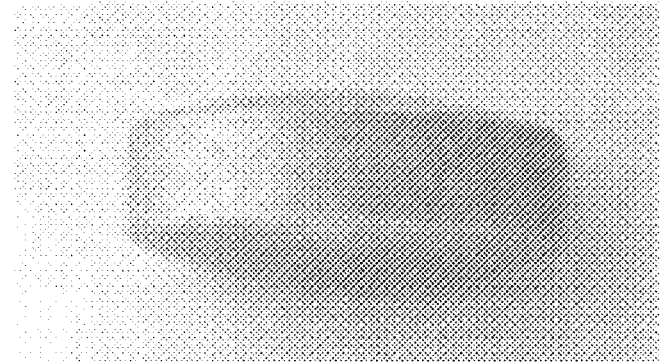
FIG. 2A shows the tablets film-coated with compositions A.

The results obtained are given in FIGS. 2A-2C, which show tablets corresponding to the tablets film-coated with compositions A, B and C, respectively.

After barely a few hours, cracking of the film-coating films was observed for the tablets film-coated with compositions B or C, i.e. using magnesium stearate, or a magnesium stearate/soyabean lecithin mixture, as plasticizer and a fluidized hydroxypropyl starch as film-forming agent.

This phenomenon is not observed for the tablets film-coated with composition A according to the invention, which comprises sorbitol as sole plasticizer.

The applicant moreover carried out other tests, using other plasticizers for film-forming compositions of fluidized hydroxypropyl pea starch.

These tests consisted in replacing the sorbitol of composition A with an equivalent amount by weight of other compounds. The results obtained can be summarized in the following way:

magnesium stearate, stearic acid, glyceryl monostearate, migliol and lecithin did not make it possible to solve the technical problems mentioned in the present invention. In particular, cracking of the films appeared systematically on the Maca tablets, before the end of the first day of incubation;

PEG 200, 400, 4000 and 6000, polyethylene glycol stearate, triethyl citrate, polysorbate, triacetin and dibutyl sebacate all result in cracking of the films during the process of film-coating the Maca tablets, so that the film-forming compositions were quite simply impossible to use.

Example 3.b)—Comparison of a Film-Forming Composition According to the Invention, with a Film-Forming Composition Using Mannitol as Plasticizer A ready-to-use product according to the invention is prepared as follows (ready-to-use 1):
Pregelatinized fluidized hydroxypropyl pea starch (hydroxypropyl group content =6.8%): 77%
Stearic acid (Stéarineries Dubois): 8%
Sorbitol (Neosorb® P60W, Roquette Freres): 15% the percentages being expressed by weight relative to the weight of solids.

The ready-to-use product according to the invention is compared with a ready-to-use product (ready-to-use 2) having the formulation:
Pregelatinized fluidized hydroxypropyl corn starch: 60%
Talc: 20%
Lecithin: 5%
Mannitol: 15%
the percentages being expressed by weight relative to the weight of solids.

Demineralized water and titanium dioxide are then added to ready-to-use 1 and 2, so as to obtain compositions at 20% solids, the titanium dioxide representing 20% of the total solids.

As soon as the aqueous film-forming composition is prepared, it is noted that the ready-to-use 1 dissolves more rapidly than the ready-to-use 2, and therefore enables easier use of the aqueous film-forming composition.

The film-coating of the Maca tablets is carried out by spraying the aqueous composition using the following equipment:
O'Hara Labcoat M perforated turbine
Film-coating turbine diameter: 8.5"
6 anti-slip bars
Spray gun: Schlick 970/7-1 S75 (nozzle diameter 0.8 mm)
Peristaltic pump: Watson Marlow model 323, head: 313 DW (3 rollers)
Exacanal tube (int. diam: 2 mm, ext. diam: 6 mm).
The operating conditions are given in the following table:

| Amount of tablets (kg) | 0.3 |
|---|---|
| Rotational speed (rpm) | 18 |
| Number of spray guns | 1 |
| Atomization pressure (bar) | 1 |
| Jet compression pressure (bar) | 1 |
| Air inlet temperature (° C.) | 50 |
| Tablet bed temperature (° C.) | 34 |

| | |
|---|---|
| Spray flow rate (g/min) | 2 |
| Spraying time (min) | 25 |
| Weight gain (%) | 3.3 |

The film-coated tablets are placed under conditions that promote deformation thereof. They are incubated without packaging at 40° C. at 75% RH.

Figure 3B:
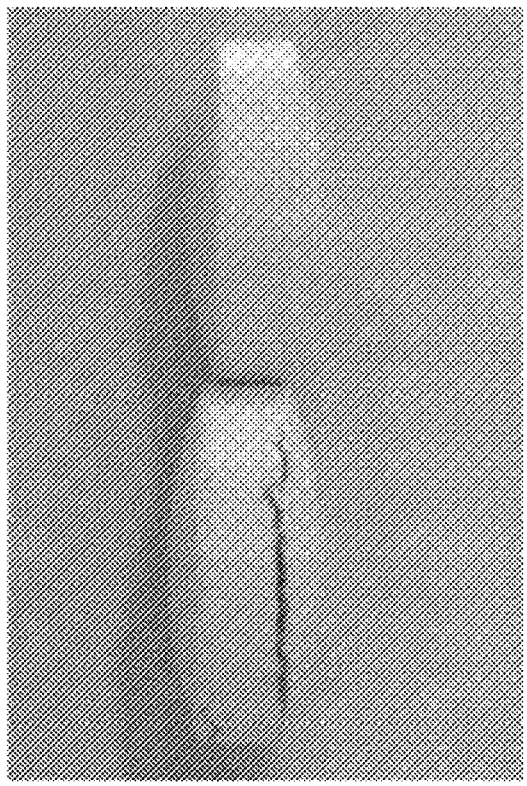
FIG. 3B shows the tablets film-coated with compositions B.
Figure 3A:
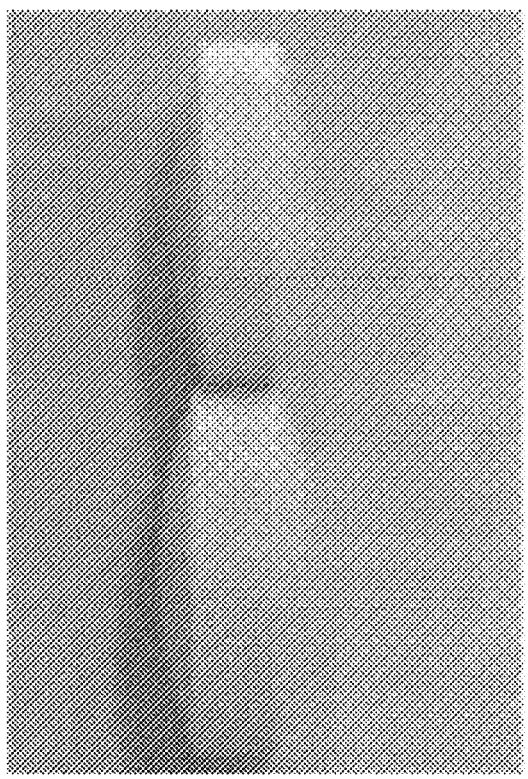
FIG. 3A shows the tablets film-coated with compositions A.

The results obtained are given in FIGS. 3A-3B, which show tablets corresponding to the tablets film-coated with compositions A and B, respectively.

Cracking of the film-coating films was observed after 5 days for the tablets film-coated with composition B, which is not produced with the tablets film-coated with composition A according to the invention.

These results confirm the superiority of sorbitol for plasticizing a fluidized hydroxypropyl starch, in particular compared with another polyol, mannitol.

The invention claimed is:

1. A film-forming composition, comprising a fluidized hydroxypropyl starch and sorbitol and in that the sorbitol is included in said film-forming composition at a content of between 5% and 40% by dry weight relative to the dry weight of fluidized hydroxypropyl starch.

2. The film-forming composition as claimed in claim 1, the fluidized hydroxypropyl starch is a corn and/or legume starch.

3. The film-forming composition as claimed in claim 1, wherein the fluidized hydroxypropyl starch and the sorbitol together represent between 15% and 100% by dry weight relative to the total weight of the solids of said film-forming composition.

4. The film-forming composition as claimed in claim 1, also further comprising an antiaggregating agent.

5. The film-forming composition as claimed in claim 1, further an opacifying agent.

6. The film-forming composition as claimed in claim 1, wherein the fluidized hydroxypropyl starch is made soluble.

7. The film-forming composition as claimed in claim 1, wherein said composition is a ready-to-use product.

8. The film-forming composition as claimed in claim 1, wherein said composition is an aqueous composition.

9. The aqueous film-forming composition as claimed in claim 8, having a solids content of between 5% and 50% by weight.

10. The aqueous film-forming composition as claimed in claim 8, having a Brookfield viscosity, at 25° C., of less than or equal to 500 mPa·s.

11. A solid form comprising a core covered with at least one film-coating layer, wherein this film-coating layer comprises a fluidized hydroxypropyl starch and sorbitol, and in that the sorbitol is included in said film-coating layer at a content of between 5% and 40% by dry weight relative to the dry weight of fluidized hydroxypropyl starch.

12. A film, comprising a fluidized hydroxypropyl starch and sorbitol, wherein the sorbitol is included in said film at a content of between 5% and 40% by dry weight relative to the dry weight of fluidized hydroxypropyl starch.

13. The film-forming composition as claimed in claim 1, wherein the fluidized hydroxypropyl starch is pea starch.

14. A film-coating process, characterized in that the process comprises:
 a step a') of spraying an aqueous film-forming composition as defined in any one of claims 8 to 10 on to a moving bed of solid forms, and
 a step b) of drying the solid forms to form film-coated solid forms.

15. A film-coating process, characterized in that the process comprises:
 a step a) of producing an aqueous film-coating composition comprising mixing a ready-to-use product as defined in claim 7 with water,
 a step a') of spraying an aqueous film-forming composition obtained in step a) on to a moving bed of solid forms, and
 a step b) of drying the solid forms to form film-coated solid forms.

16. The film-coating process as claimed in claim 14, characterized in that the bed of solid forms is preheated to a temperature of between 30 and 60° C.

17. The film-coating process as claimed in claim 15, characterized in that the bed of solid forms is preheated to a temperature of between 30 and 60° C.

* * * * *